United States Patent [19]

Fawcett et al.

[11] Patent Number: 4,821,303
[45] Date of Patent: Apr. 11, 1989

[54] COMBINED THERMAL ANALYZER AND X-RAY DIFFRACTOMETER

[75] Inventors: Timothy G. Fawcett; William C. Harris, Jr.; Robert A. Newman; Lawrence F. Whiting; Frank J. Knoll, all of Midland, Mich.

[73] Assignee: The Dow Chemical Company, Midland, Mich.

[21] Appl. No.: 105,769

[22] Filed: Oct. 6, 1987

Related U.S. Application Data

[63] Continuation of Ser. No. 938,682, Dec. 5, 1986.

[51] Int. Cl.⁴ .......................................... G01N 23/20
[52] U.S. Cl. ...................................... 378/80; 378/71
[58] Field of Search ............... 378/70, 71, 80; 374/31, 374/33, 34

[56] References Cited

U.S. PATENT DOCUMENTS

| | | | |
|---|---|---|---|
| 3,051,834 | 8/1962 | Shimula et al. | 378/80 |
| 3,263,484 | 8/1966 | Watson et al. | 73/15 |
| 3,337,731 | 8/1967 | Kinznetsov et al. | 378/80 |
| 4,263,510 | 4/1981 | Ciccarelli et al. | 378/80 |

FOREIGN PATENT DOCUMENTS

| | | |
|---|---|---|
| 923025 | 4/1963 | United Kingdom. |
| 936910 | 9/1963 | United Kingdom. |
| 945788 | 1/1964 | United Kingdom. |
| 1432826 | 4/1976 | United Kingdom. |
| 2079465A | 1/1982 | United Kingdom. |

OTHER PUBLICATIONS

"Purity Determination by Simultaneous DSC-Thermomicroscopy", by Wiedemann et al.
"Simultaneous ... of Melting and Freezing Processes", by Van Ters et al., Mettle Instrument A.G.
"Simultaneous Differential Scanning Calorimetry and Small α Angle X-Ray Scattering", by Russell et al., Journal of Polymer Science Polymer Phys. Ed., vol. 23 (1985).
Thermochimica Acta, vol. 7 (1973), pp. 131-149, H. G. Wiedemann, "Thermal Analysis and Synthesis of Pentazinc Hexahydroxide Dicarbonate-Investigations by Thermogravimetry, Thermo Molecular Beam Analysis and X-Ray Measurements".
Analytical Chemistry, vol. 266 (1973), pp. 97-109, H. D. Wiedemann and G. Bayer, "Investigation of Minerals and of Lunar Samples (14163, 14258) by Simultaneous Thermal and X-Ray Analysis".
Journal of Physics E, vol. 7, No. 7 (1974), pp. 509-510, N. Gerard, "Coupling of Thermogravimetric and X-Ray Diffraction Methods".
Thermochimica Acta, vol. 59, No. 3 (1982), pp. 343-359, P. J. Haines and G. A. Skinner, "Simultaneous Differential Scanning Calorimetry and Reflected Light Intensity Measurement".
Advances in X-Ray Analysis, vol. 22, Plenum Press, New York and London (1979), pp. 255-265.
H. E. Göbel, "A New Method for Fast XRPD Using a Position Sensitive Detector".

(List continued on next page.)

Primary Examiner—Craig E. Church
Assistant Examiner—John C. Freeman
Attorney, Agent, or Firm—Burke M. Halldorson

[57] ABSTRACT

Scientific apparatus and a method are described for observing simultaneously both structural and thermodynamic properties of materials. An X-ray diffractometer and a thermal analyzer and mounted to cooperate and coact on the same sample and to complete a meaningful analysis in a very few minutes. The diffractometer is equipped with a rapid position-sensitive detector connected to a multichannel analyzer to record and display X-ray diffraction data from the sample over an angle of 20°·(two theta) or more. The thermal analyzer is preferably a differential scanning calorimeter. By correlating X-ray diffraction and thermal data taken simultaneously while the sample is passing through a range of temperatures and/or environments, structural changes corresponding to thermal events can be identified and elucidated.

9 Claims, 14 Drawing Sheets

OTHER PUBLICATIONS

Analytik Systematischer Überblick, Dr. Klaus Danzer et al., (Leipzig, 1976), Akademische Verlagsgesellschaft, Chapter 3.34 (pp. 135–136) and Chapter 4.4.1 (pp. 258–264).

Analytical Chemistry, vol. 36, No. 7, Jun. 1964, pp. 1233–1238, E. S. Watson et al., "A Differential Scanning Calorimeter for Quantitative Differential Thermal Analysis".

Analytik Systematischer Überblick, Dr. Klaus Danzer et al., (Leipzig, 1976), Akademische Verlagsgesellschaft, Chapter 3.3, pp. 125–135.

Patent Abstracts of Japan, vol. 8, No. 101, May 12, 1984, p. 129P273, JP 59-13945 (1-24-84).

Patent Abstracts of Japan, vol. 6, No. 188, Sep. 28, 1982, p. 29P144, JP 57-98847 (6-19-82).

Advances in X-Ray Analysis, vol. 25, 1982, pp. 315–324, H. E. Göbel, "A Guinier Diffractometer with a Scanning Position Sensitive Detector".

The Journal of Vacuum Science & Technology, vol. 9, No. 2 (Mar./Apr. 1972), pp. 600–602, A. Benninghoven et al., "Simultaneous SIMS, EID and Flash-Filament Investigations of the Interaction of Gases with a Tungsten Surface".

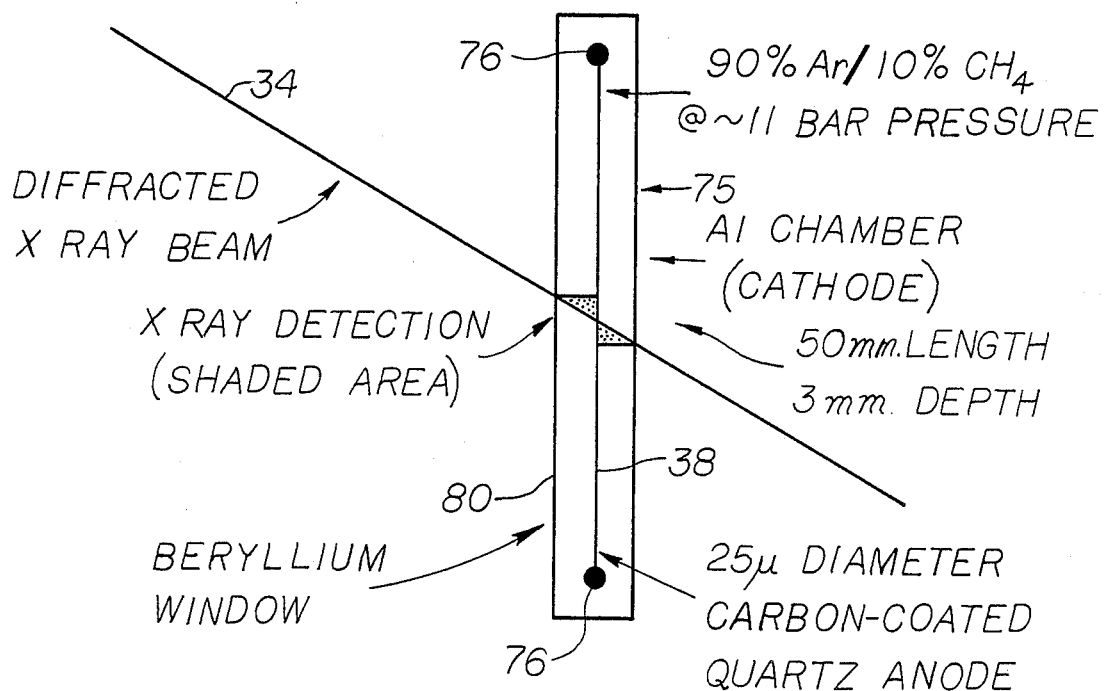
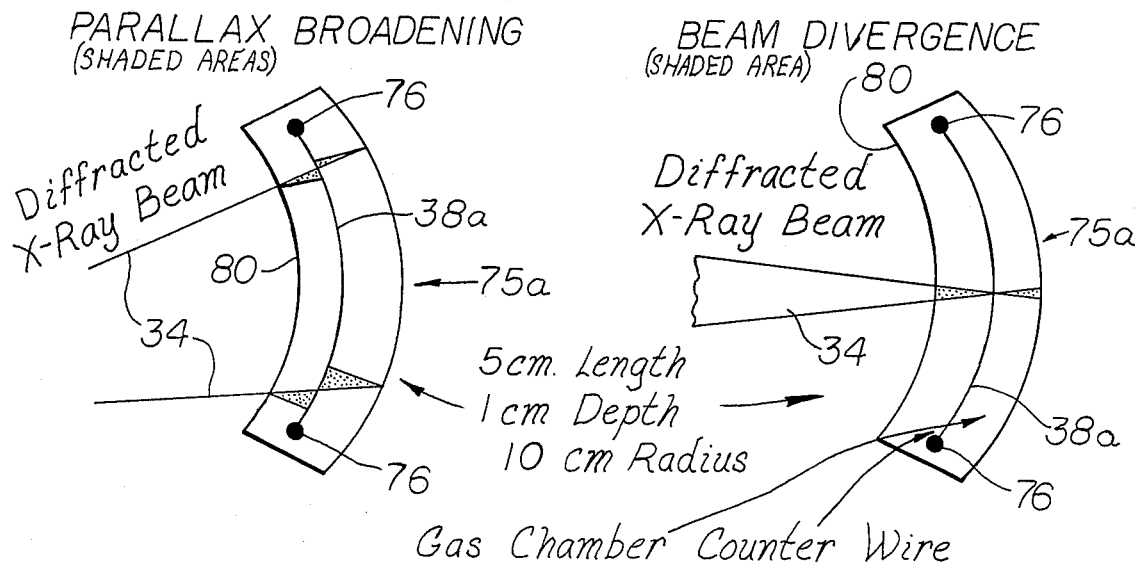

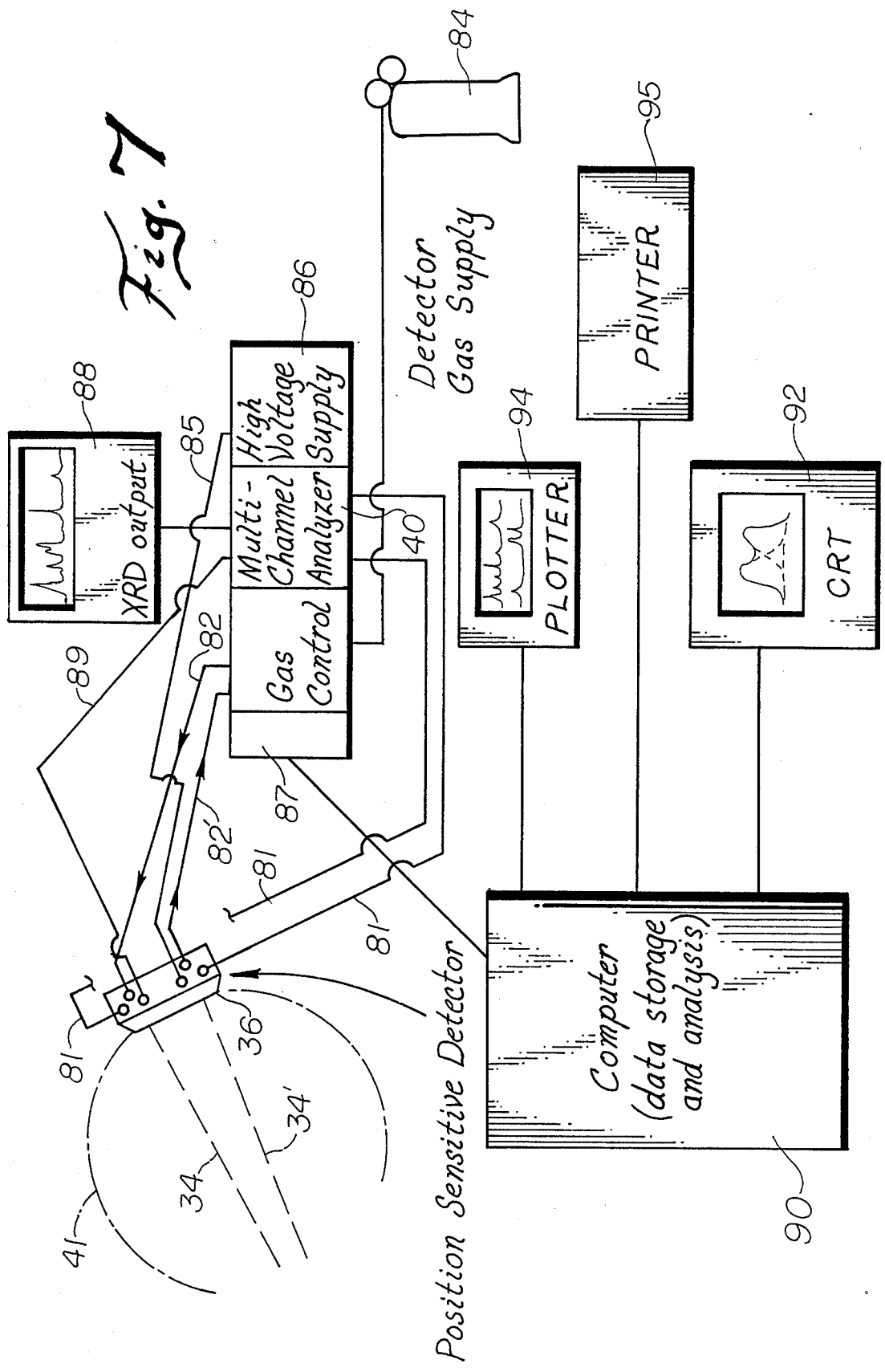

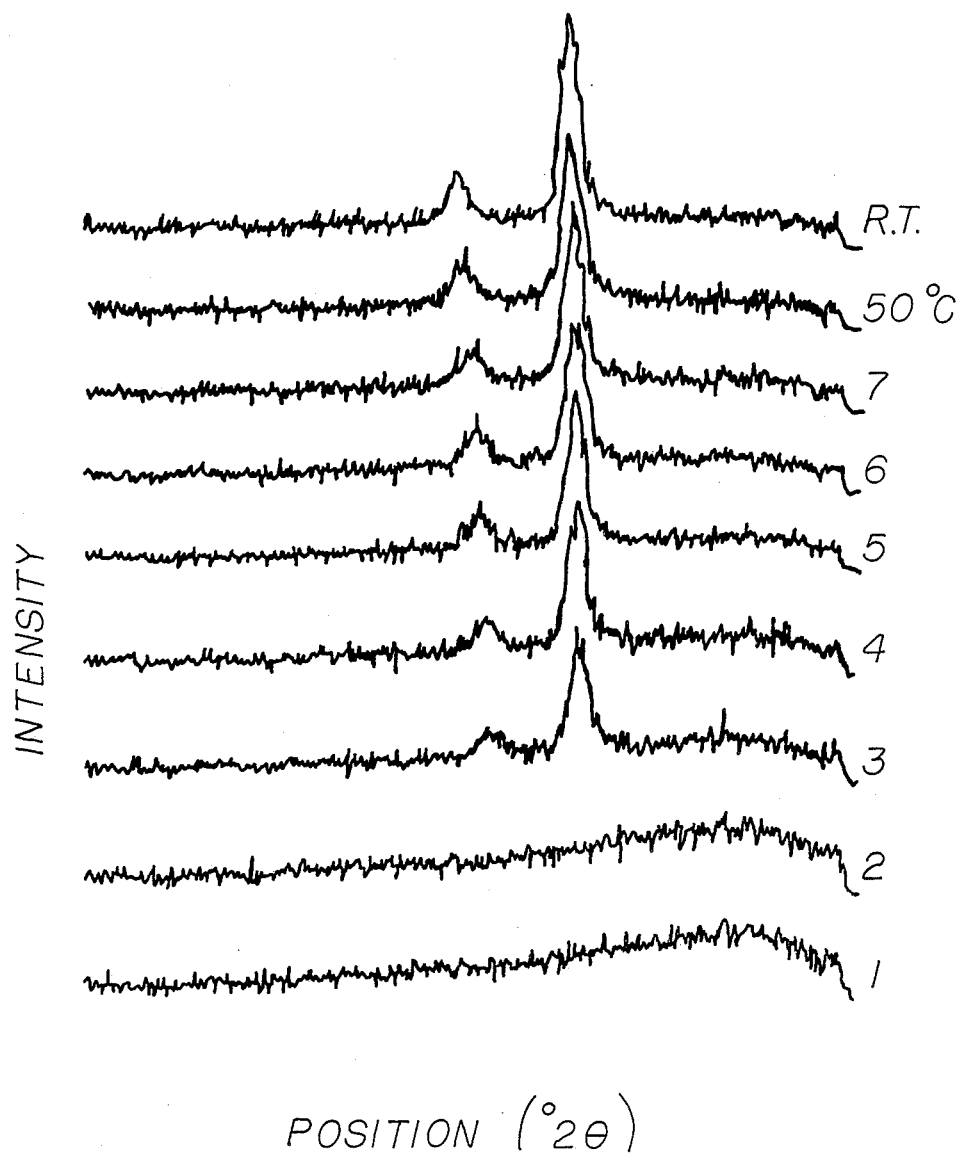

Fig. 14 a-c
DSC scan from 140-150°C showing in successive scans a polymorphic interconversion of a low melting polymorph to a higher melting structure.

Rapid 20°/min. scan of original sample

Rapid 20°/min. scan of the sample after the interactive experiment

Interactive DSC/XRD experiment used to interconvert forms I and II. The material was successively heated, held isothermally for 3 minutes, then heated to a slightly higher temperature, held for 3 minutes, etc... Only selected X-ray diffraction data (at 1 and 2) corresponding to this DSC scan are shown in Fig. 15.

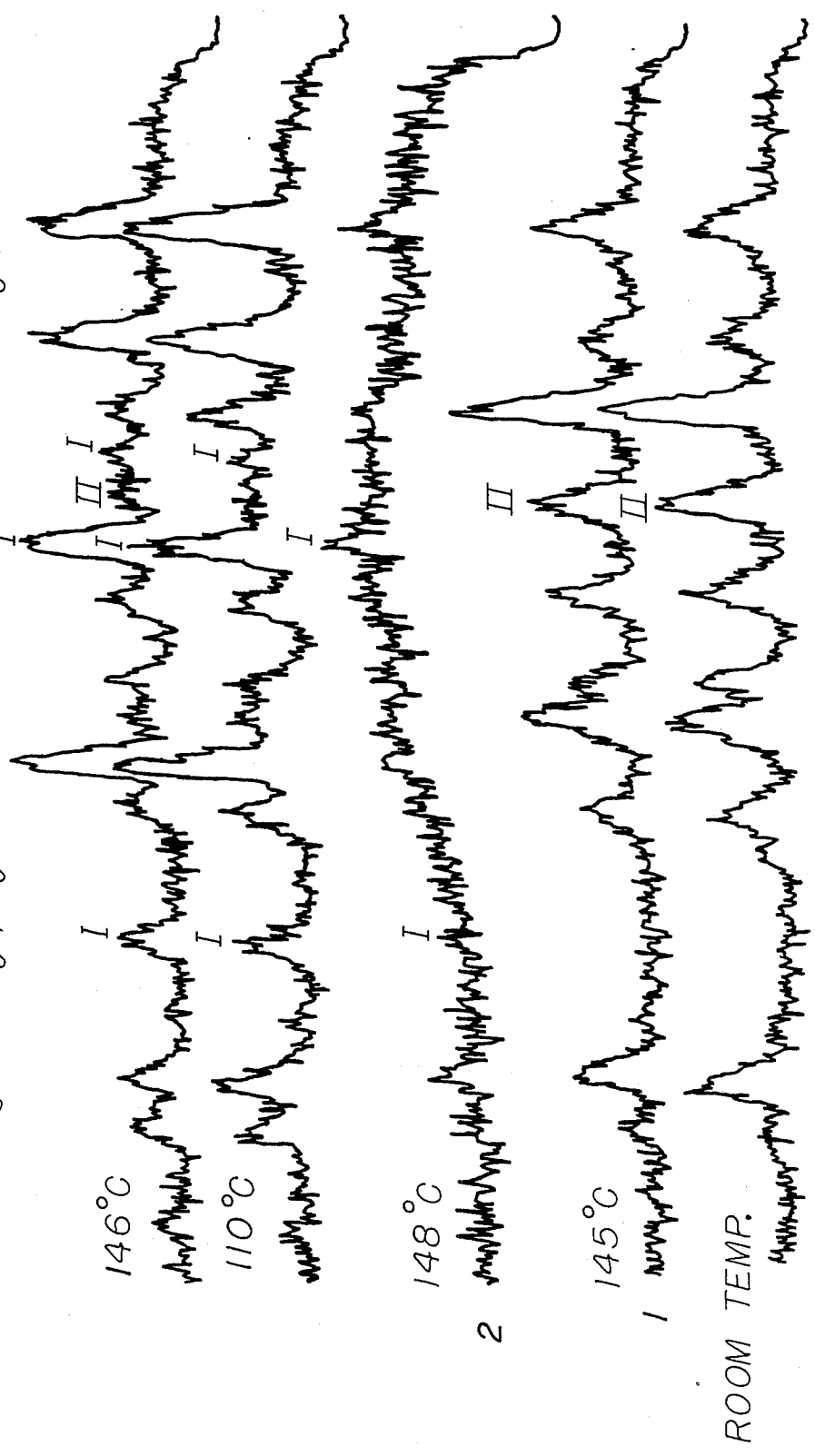

COMBINED THERMAL ANALYZER AND X-RAY DIFFRACTOMETER

CROSS REFERENCE TO RELATED APPLICATION

This is a continuation of application Ser. No. 938,682, filed Dec. 5, 1986.

FIELD OF THE INVENTION

This invention relates to a scientific apparatus and a method for observing thermodynamic and structural properties of materials. It particularly concerns an instrument for simultaneous calorimetric and X-ray diffraction analysis.

BACKGROUND OF THE INVENTION

In characterizing the physical and chemical behavior of substances, it is customary to separately investigate both their thermodynamic (e.g., calorimetric) and their structural (e.g. crystallographic) properties.

Thermodynamic properties are commonly determined by differential scanning calorimetry (DSC) and by differential thermal analysis (DTA). Modern DSC and DTA instruments are highly advanced, affording sensitive temperature regulation and measurement, often to a fraction of a Centigrade degree. A sample may be heated rapidly through a wide temperature range, and calorimetric output measured with precision, over a period of a very few minutes.

Crystallographic properties are often studied by X-ray diffraction (XRD) spectrometry. To achieve high resolution, diffraction data have been collected on photographic film, or with scintillation counters. Such procedures are slow, requiring data collection times of thirty minutes or more for each pattern at each temperature. A single scan over a range of temperatures may consume most of a day or longer. Because of the slow data collection times for X-ray diffraction scans, structural and calorimetric data could not be correlated for fast processes. In industrial processes, heat and/or chemical treatments often occur in a matter of a few minutes or seconds (i.e. the extrusion of a polymer or the oxidation of a catalyst). In addition, the equipment for heating samples in X-ray diffraction analysis has been comparatively crude, e.g., uniform sample temperature control within five degrees has been attainable only rarely except near room temperature. For both reasons, rapid scanning, i.e., dynamic reading of a series of X-ray diffraction patterns correlated accurately and simultaneously with temperature rise as a sample is heated, has not been previously practiced.

Instead, the usual approach has been to analyze a sample first by one of the foregoing techniques and then by the other. Data from the two determinations were correlated as best might be, to elucidate as far as possible the thermostructural behavior of the sample. However, due to the differences in sample heating conditions and sample size, and in the data collection times between DSC and conventional XRD, the diffraction and calorimetric data did not correlate well when trying to assign an observed structural change to a particular calorimetric event. In applying this method to multicomponent samples, separate physicochemical phenomena occurring at closely spaced temperatures were often missed or misinterpreted as were indications of transitory species and irreversible phase changes occurring over a period of a minute or two.

More recently, one aspect of this situation has been improved. Position sensitive detectors have been developed as X-ray detectors, dramatically increasing the speed of acquiring diffraction data. With them, the time scale for X-ray diffraction analysis can be shortened to be compatible with that of differential thermal analysis and differential scanning calorimetry.

The present invention takes advantage of this improvement and provides a workable instrument and method for simultaneous dynamic observation of thermodynamic and structural properties of a sample undergoing temperature and/or environmental change.

SUMMARY OF THE INVENTION

The instrument of the invention includes in combination both an X-ray diffractometer and a thermal analyzer (either a differential scanning calorimeter or a differential thermal analyzer) mounted to cooperate and simultaneously coact on the same sample undergoing analysis. The diffractometer includes a source of an X-ray beam directed to impinge on a sample also being acted upon and observed for determination of certain thermodynamic properties, and a rapid position sensitive detector to receive radiation diffracted from the sample to determine structural properties. The thermal analyzer includes within a sample holder assembly, a sample holder on or by which means the sample is positioned and retained for the joint analysis. The sample holder assembly has an inlet port or X-ray transparent window positioned to allow the diffractometer X-ray beam to strike the sample in the holder and an outlet slit or window to allow passage of diffracted radiation to the X-ray detector. The analyzer also includes control means for changing the temperature of the sample in the holder and means for observing the thermodynamic behavior of the sample during such change.

The X-ray source preferably provides a focused monochromatic beam. Advantageously, it is a line source equipped with a Guinier diffraction system and a curved focusing monochromator. The source and the sample holder (and the surrounding enclosure) are arranged geometrically so that a sample in the holder lies at a point along the focusing circle of the diffractometer.

The X-ray detector is preferably a position-sensitive proportional counter mounted for movement about the focusing circle of the diffractometer with the sensitive element placed along the arc of the circle. The detector is connected to electronic readout circuitry. This may include a multichannel analyzer with a display terminal or recorder to indicate numerically and graphically the positions and intensities of the lines forming the X-ray diffraction pattern.

The thermal analyzer is preferably a differential scanning calorimeter provided with electronic readout circuitry to display and record both the temperature of the sample throughout analysis and the existence and magnitude of calorimetric events occurring in the sample. The circuitry also contains means for controlling the temperature of the sample in the holder. Beneficially, this means is programmable to increase, decrease or hold the temperature.

As a non-limiting example, the sample holder assembly (sometimes referred to as the specimen holder assembly or cell) may comprises a protective enclosure, conveniently a metal block with a cover to seal the interior tightly. The block contains two chambers (or alternatively a single common chamber) for the sample and reference holders.

More broadly, various different sample holder assembly designs than that specifically described are known and may be alternatively employed, e.g., as illustrated by the literature and DSC and DTA commercial instruments made reference to herein. Similarly, the sample holder may take numerous forms, modified where required to permit the simultaneous analysis of sample contemplated by the invention.

For sealed operation, the X-ray transmitting inlet port and outlet slit of the sample holder assembly are made into windows by covering them with a thin sheet of X-ray transmitting material. If the instrument is to be used to study the effect of a particular gaseous medium on a test sample undergoing analysis, the sample holder assembly may also be provided with inlet and outlet means for controllably passing gas through it and into contact with the sample.

Besides providing a novel instrument, the invention also resides in a method of simultaneously analyzing the thermodynamic and structural properties of materials. In this method, a sample of the material is subjected to a program of temperature and/or environment change. During the program, e.g., in the DSC mode, the differential heat flow into and out of the sample indicative of calorimetric behavior is observed throughout. At the same time, the sample is exposed to a focused X-ray beam and diffraction data from the sample are also observed throughout. The calorimetric data and X-ray data are then compared as functions of temperature and environment. This comparison affords great insight into the fundamental physicochemical behavior of the sample, and, in the case of a multicomponent sample, also of the substances composing it and how these materials may interact with each other.

The instrument and method may be operated over a very wide range of temperatures and with a variety of atmospheres. They can scan and record calorimetric and X-ray diffraction data simultaneously while the sample is heated through an interval of several hundred degrees, and do it all in a few minutes. X-ray data are recollected dynamically as thermal analysis proceeds, providing direct correlation of structural change with brief transient calorimetric events. The kinetics of thermally and atmospherically induced structural transformations can be investigated with precision, making possible interpretation of complex DSC curves. In samples containing several components, phases can be readily distinguished and calorimetric events assigned with assurance to individual components or to reactions between two or more components. Results of this character have not heretofore been achieved.

BRIEF DESCRIPTION OF THE DRAWINGS

The invention may be explained with reference to the accompanying drawings, in which

FIG. 5 is a schematic sectional view of a linear position sensitive proportional counter used as an X-ray detector as shown in FIG. 1.

FIGS. 6a and 6b are schematic sectional views of a curved position sensitive proportional counter which may be used as an alternative to the counter of FIG. 5. The figures also show the common errors associated with these types of detectors.

FIG. 7 is a block diagram showing schematically the detector control and recording systems of the X-ray diffractometer portion of the instrument according to the invention.

FIGS. 13a and 13b are similar to the recording of FIGS. 12a and 12b, respectively, except made during a cooling cycle.

FIG. 15 - X-ray diffraction patterns made with the apparatus of the invention showing the interconversion of the lower melting to the higher melting polymorph.

DETAILED DESCRIPTION OF THE INVENTION

Figure 1:
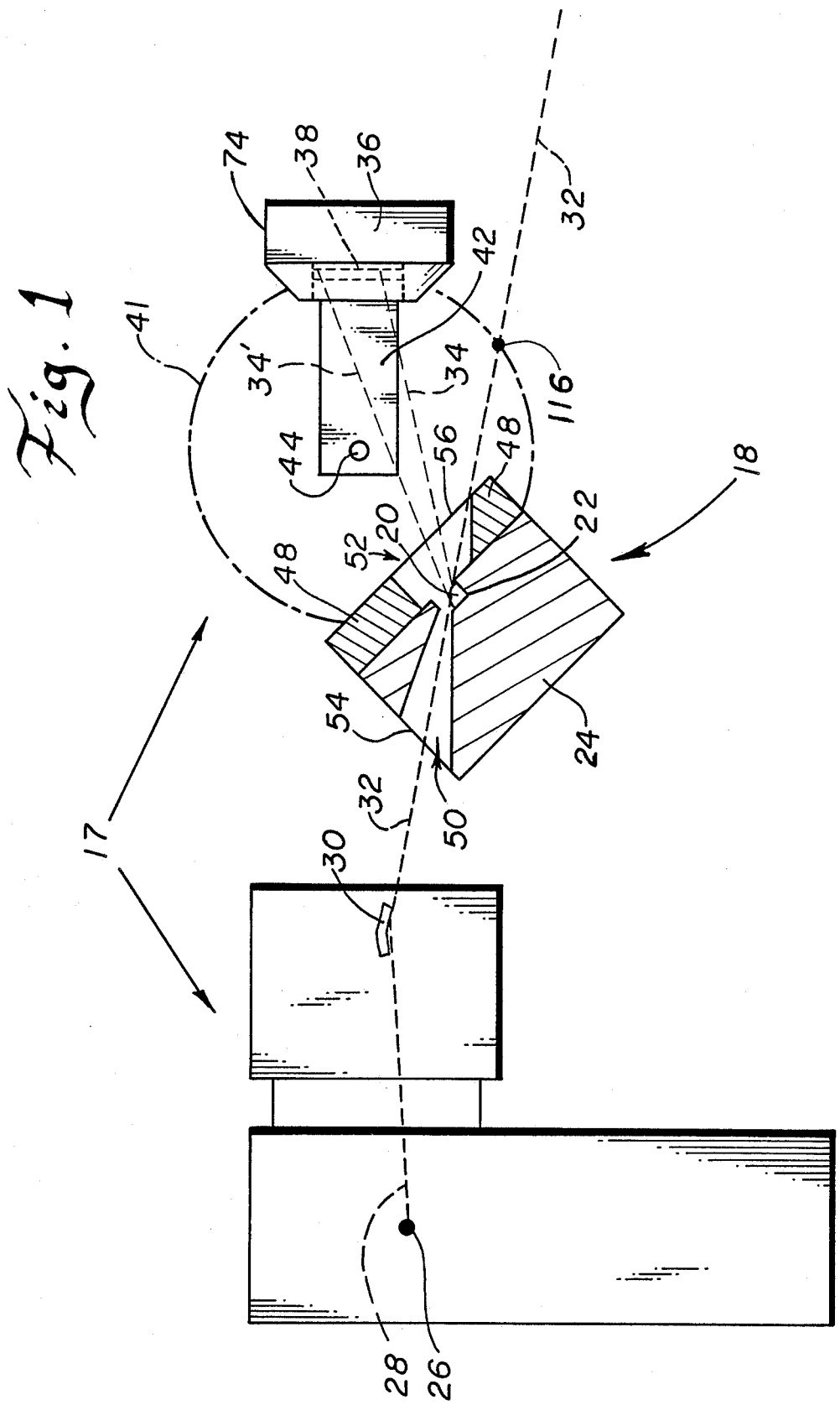
FIG. 1 is a schematic plan view of a combined X-ray diffractometer and differential scanning calorimeter according to the invention, omitting the electronic control and recording systems. The view shows the instrument in the geometry of the Huber-Guinier system.
Figure 2:
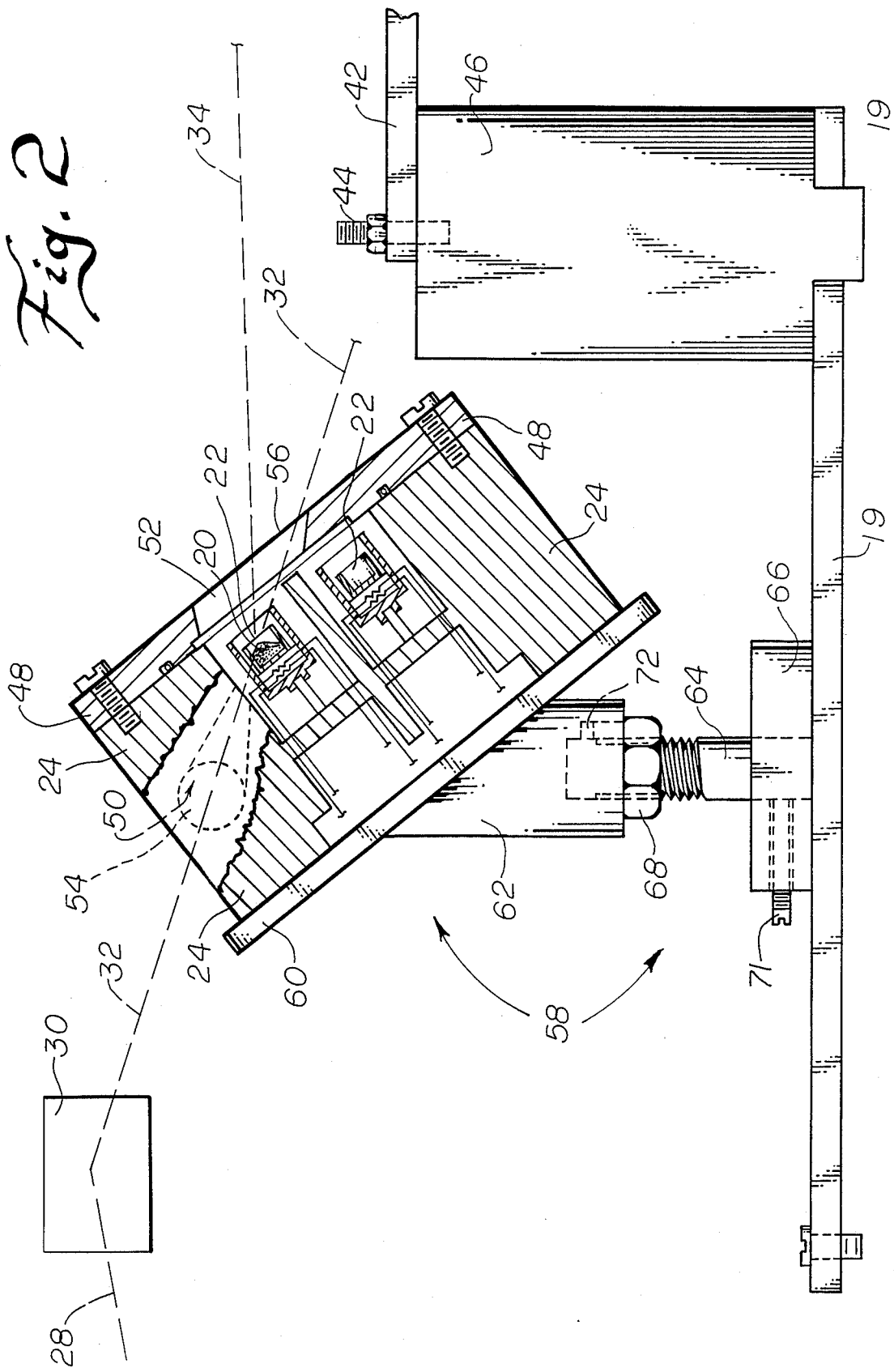
FIG. 2 is an elevational view, partly schematic, of the central part of the instrument of FIG. 1, enlarged to show the sample enclosure and its mounting.

The basic elements of the invention, in a preferred form, are shown schematically in FIGS. 1 and 2. They include an X-ray diffractometer, indicated generally as 17, and a differential scanning calorimeter, the sample holder assembly of which is indicated generally as 18. They are grouped together closely and are mounted on a common base 19 for alignment and positioning purposes as will be described further below.

A sample 20 of material to be studied is held in a small pan 22 or crucible, e.g., of aluminum foil, and placed in a sample holder 96 within the sample holder assembly 18. Only milligrams of the material, usually as powder or film, are required. The sample holder assembly of the block design mentioned previously is made from a protective enclosure block 24 taken from a commercial instrument. However, it is modified and placed so that it also serves as the sample support of the X-ray diffractometer. In this way, the diffractometer 17 and calorimeter 18 share the sample in common and study it simultaneously.

(A) Diffractometer

In the diffractometer 17, a source 26 produces a beam 28 of X-rays which impinges on a monochromator 30. This latter disperses and redirects the X-rays, providing a monoenergetic beam 32 which converges on the sample 20. The X-radiation passes through the sample, and a part is diffracted away from the main beam at various fixed angles. Two are shown in FIG. 1 as 34 and 34'. The diffraction or "scattering" angles, conventionally called $2\theta$ (two theta), and the corresponding intensities of the diffracted X-rays, are characteristic of the crystal structure(s) of the sample. The diffracted X-rays are collected by a position sensitive detector 36. Detector 36 registers the arrival of diffraction radiation and also provides information about where along its length (one-dimensional detector) or over its area (two-dimensional detector) the radiation was absorbed. See also the transactions of The American Crystallographic Association, Vol. 18, 1982, page 9, R. C. Hamlin, Ed.

This detector is of known design and includes a 25 micron diameter wire 38 for sensing the angular positions and frequency (i.e., counts/sec) at which incident X-ray photons enter. The detector, which covers an angular range of about 20° two theta, is connected to a multichannel analyzer 40 (FIG. 7). This latter stores the output data indicating angular position and intensity of the diffraction data. The detector and analyzer are further described below.

Both the test sample 20 and the detector 36 are positioned so that they lie in a horizontal plane on the circumference of the focusing circle 41 of the X-ray diffractometer (dashed circle in FIG. 1). At all points along the circle, the X-rays are at their best focus and resolution of the diffraction data is at its highest. The position of the sample 20 stays fixed, but the detector 36 is mounted on a bracket 42 pivoted about a post 44. The post is screwed into a mounting block 46 held adjustably on the base 19 by means not shown. The mount 46 is positioned so that the post 44 is at the center of the focusing circle 41. In this arrangement, the detector may be revolved to successive positions along the focusing circle when it is desired to observe data over an angular range greater than that subtended by the detector in a single location.

Figure 3:
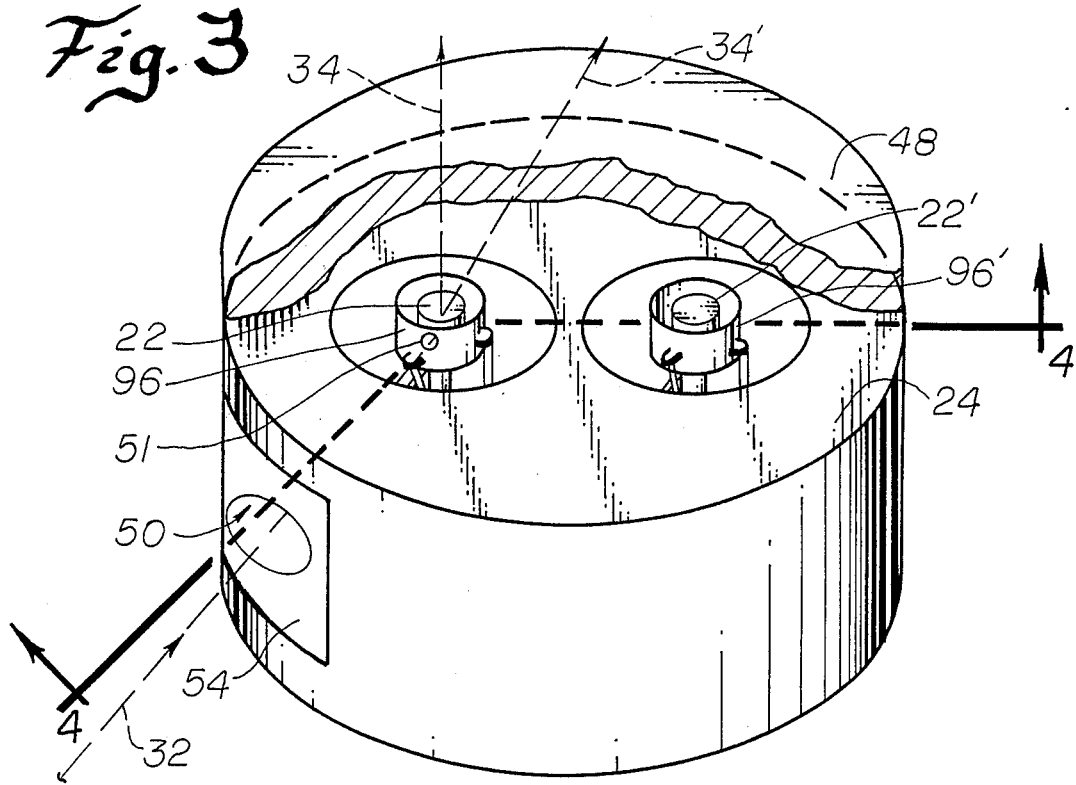
FIG. 3 is a cutaway perspective view of the sample enclosure of FIG. 2.
Figure 4:
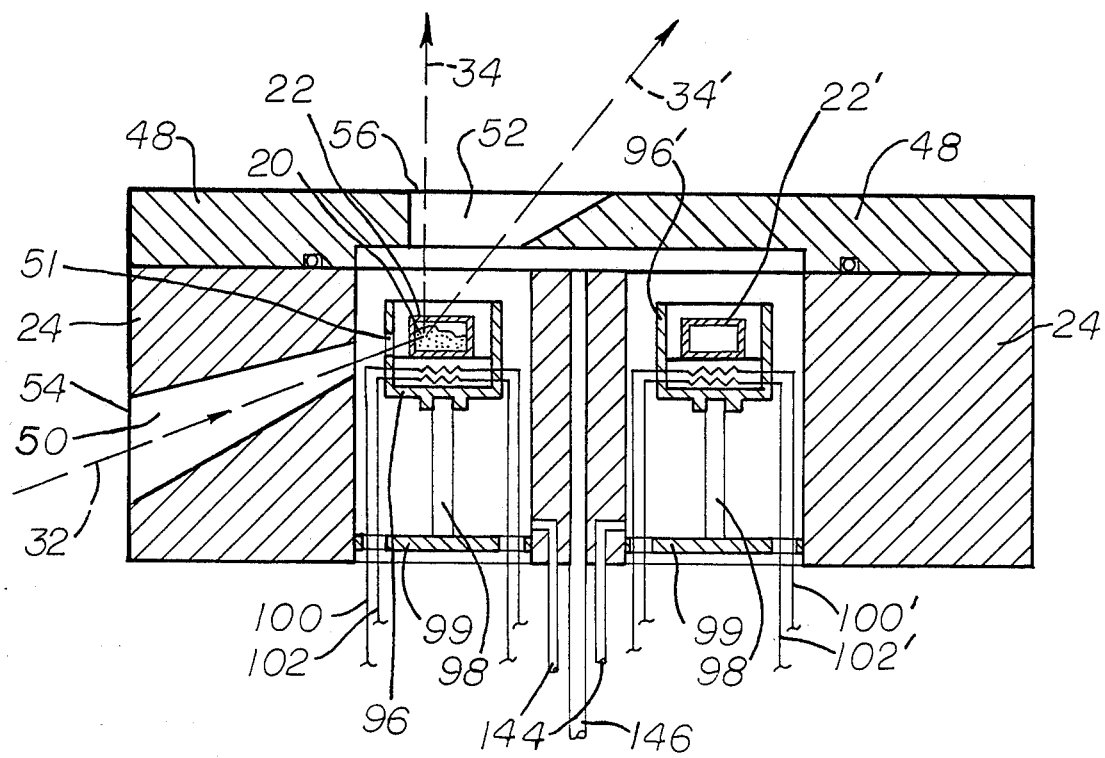
FIG. 4 is a schematic sectional elevation of the sample enclosure, taken along the line 4—4 in FIG. 3, showing the sample holder with associated heating and temperature sensing elements. The figure also shows the gas port inlets and outlet.

The enclosure block 24, which supports the sample 20 in the path of the X-ray beam 32, is closed by a cover 48. To allow passage of the X-rays, the wall of the block 24 and the cover 48 are machined out to form an inlet port 50 for incoming X-radiation and an exit slit 52 for the X-radiation (FIGS. 2 to 4). The port 50 is tapered conically, narrowing down inwardly to minimize intensity loss of the converging X-ray beam 32 toward the sample. A small hole 51 is machined in the side of sample holder 96 near the location of the sample pan 22 to allow X-rays to impinge directly upon the sample 20. The sample holder cover (not shown) which is normally placed on top of the sample holder 96 must be modified or removed, as in this case, to permit the diffracted X-rays to exit the sample holder 96 and enclosure block 24. For optimum DSC heat measurement sensitivity, the X-ray inlet port 51 and the sample holder top may be covered with an X-ray transmitting material which will help to minimize unwanted radiative and convective heat transfer from the sample. Additionally, when the chamber in the block is to be kept gas-tight, the inner and outer ends of the inlet port and of the exit slit are covered with thin films 54 and 56 of X-ray transmitting material, such as a sheet of beryllium or of Mylar (polyethylene terephthalate plastic). Mylar windows have the advantage that the sample can be visually observed at any time during an experiment if the sample pan is not covered.

For positioning the sample 20 in the X-ray beam, the sample holder assembly 18 is made adjustable in all dimensions by securing it to a mounting assembly (generally 58 in FIG. 2) which rests on the adjustable instrument base 19. The block 24 of the sample holder assembly sits on a plate 60 tilted so that the X-ray beam 32 can impinge at an angle on the sample 20. The tilt also provides a good thermal contact between the sample pan and the sample holder 96. The plate is secured adjustably to a pillar 62. This latter is socketed and is pinned at 72 to a threaded post 64 seated at its other end in a mount block 66. A nut 68 allows vertical adjustment. For lateral adjustment, the mount block may be slid relative to the base 19, to which it is held by screws. The sample holder assembly may be pivoted to a desired position and locked in place by a locking screw 71.

In a preferred embodiment of the invention, the X-ray detector 36 is a linear position sensitive proportional counter, a commercially available unit. It is shown schematically in FIG. 5. Briefly, this detector has an elongated shallow box-like housing 74. Terminals 76 insulated from the housing support a single straight anode counter wire 38, a carbon-coated quartz fiber of high resistance. High voltage is applied between this wire and one or more cathode elements 75 paralleling it. Diffracted X-ray photons 34 enter the counter through a beryllium window 80 and initiate gas ionizations which characterize their entrance positions along the counter wire. External circuitry supplies the required voltage and records the angular positions and the intensities of tee diffracted X-rays. A gas mixture, such as argon-methane or xenon-methane, may be passed under pressure through the housing by way of an inlet 82 and an outlet 82' (FIG. 7) to maintain in known manner the levels of sensitivity and efficiency of the detector.

Instead of the linear detector just described, an alternative, also useful in the invention, is a curved detector as shown in FIGS. 6a and 6b. Here the housing 75a is of arcuate shape and supports a curved counter wire 38a. One such curved counter is described in U.S. Pat. No. 4,076,981. Various position sensitive detectors optimize either speed, detection area or resolution. Depending on the particular experiment, one type of detector may be preferred over another (e.g., for a detailed discussion of common errors associated with these detectors, see Reference (1), below). For illustrative purposes, the following references describing these detectors are lifted and fully incorporated into this disclosure:

(1) R. A. Newman, T. G. Fawcett, P. M. Kirchhoff, Advances in X-ray Analysis, Vol. 27, 1984 (in press).

(2) H. E. Göbel, Advances in X-ray Analysis, Vol. 22, 1979, p. 255–265.

(3) H. E. Göbel, Advances in X-ray Analysis, Vol. 25, (1982), p. 315–324.

(4) C. O. Ruud, Industrial Research and Development, January, 1983, p. 84–87.

(5) Proceedings of the Symposium on New Crystallographic Detectors, Transactions of the American Crystallographic Association, Vol. 18, 1982, R. C. Hamlin, Ed.

The control and display apparatus associated with the detector 36 is shown diagrammatically in FIG. 7. The gaseous atmosphere in the detector comes from a supply 84 which regulates flow and pressure. The high voltage of the sensing wire 38 is delivered by a source 86. The X-ray output data from the detector are stored in a digital analyzer 40 in about 1500 discrete channels, each corresponding to a location along the wire 38. Thus, the detector and analyzer together observe incident X-ray photons and record the diffraction data as angular positions or addresses at which the diffracted photons enter the detector chamber and the number of such incidents at each location. With a detector covering an angular range of 20° two theta an analyzer recording 1500 channels can discriminate between angles of incidence with a selectivity of about 0.8 minute of arc.

For instantaneous observation, the analyzer is connected to a video terminal 88 which displays graphically the data accumulating in the analyzer. The raw data also go to a computer 90. This latter may be programmed with peak-fitting and data-reduction routines, smoothing and background-suppressing algorithms, etc., to record and output parameters such as angular positions and magnitudes of peak intensities, peak areas and half-widths, and other desired parameters. The computer output is displayed on a video terminal 92 and recorded on a plotter 94 or printed on a printer 95. The resulting diffraction data, in which the intensities of X-ray diffraction lines are plotted as a function of diffraction angles, as in FIG. 15, constitutes the ultimate data output of the diffractometer part of the instrument of the invention.

The detector and the control and read-out equipment are all available commercially. The method of using this detector and of interpreting results are known. For more description of detector-counters and appropriate circuitry, see N. Broll, M. Henna, and W. Krantz, Siemens Corporation Application Note No. 57, September 1980, Cherry Hill, N.J.; and Analytical Application Notes No. 271 from Innovative Technology, Inc., South Hamilton, Mass.

(B) Differential Scanning Calorimeter

At the heart of the calorimeter, shown in FIGS. 2 to 4, the sample 20 and its pan 22 are placed inside the sample holder 96 which is mounted inside a chamber in the aluminum block 24 mentioned above as a part of the diffractometer. This block also forms the protective chamber and temperature controlled environment of the calorimeter. The block may include an attachment, not shown, for circulating fluid to cool or heat it. The chamber may be made gas-tight by its cover 48.

Figure 9:
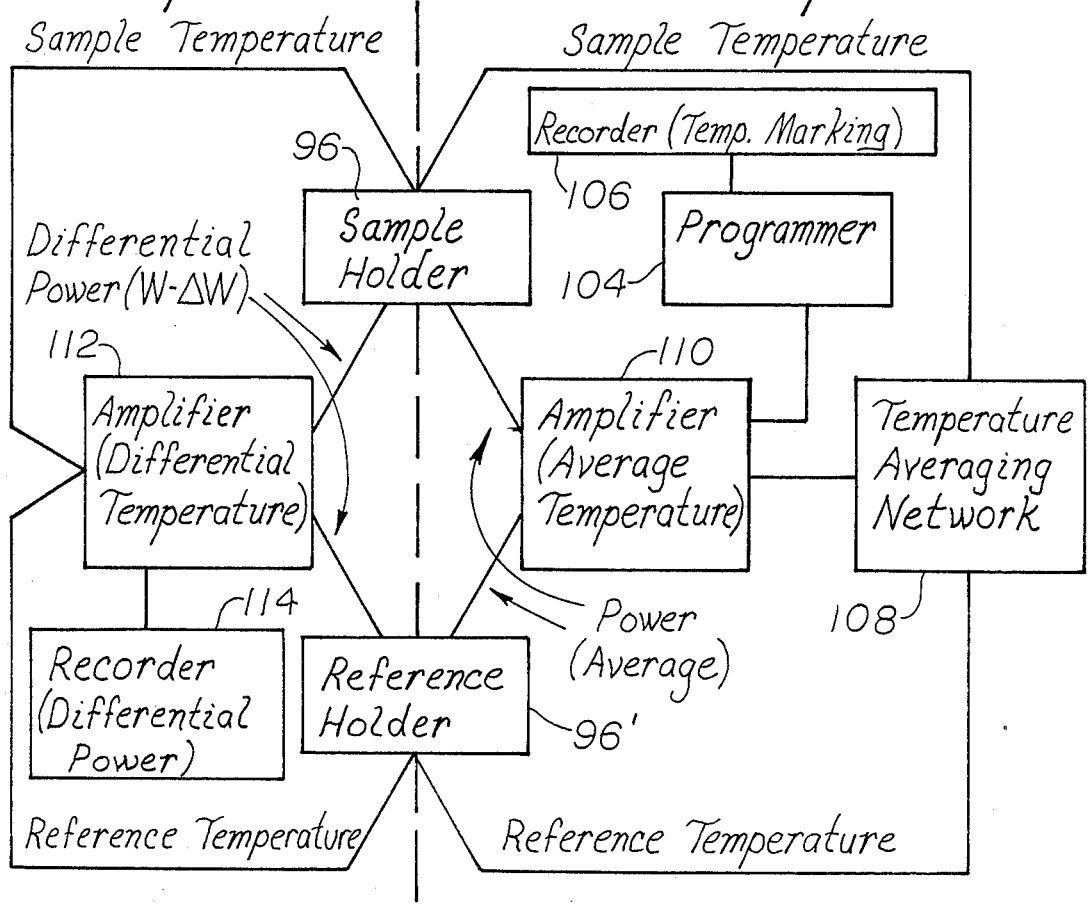
FIG. 9 is a block diagram of the electronic sensing and control systems of the differential scanning calorimeter forming another portion of the instrument of the invention.

Within the block 24, the sample pan 22 rests on a thermally conducting sample holder 96 (FIG. 4). The holder, supported by a center post 98 mounted on a holder support disc 99, includes a resistive heating element 100 and a resistive temperature-sensing element 102 in close proximity. These elements are connected by leads to electronic control and sensing circuits shown diagrammatically in FIG. 9. Also within the block 24 is a reference or matching holder assembly (shown generally as 96') supporting an optional calorimetric reference specimen (not shown) in a matching pan 22'.

In a known mode of operating the differential scanning calorimeter of the general type shown, the same "average" power is supplied to both the heating elements 100 and 100' to control continuously the temperatures of the sample and reference material gradually through the range of temperatures over which the thermal behavior of the sample is to be analyzed. The temperatures indicated by the two thermometric elements 102, 102' are observed throughout the scan by the control system, which also acts to maintain them in equilibrium by applying the necessary amount of power to the heating elements. When an endothermic event occurs in the sample, the control system supplies more differential power to the sample to keep the sample and reference temperatures in equilibrium. When an exothermic reaction occurs, less differential power is applied to the sample. The magnitude of this differential power is a measure of the magnitude of the physical or chemical process. Its value, shown by the instrumentation described, is one of the major parameters or outputs of the apparatus of the invention.

In the control system (FIG. 9), the programmer 104 (with its associated temperature recorder 106) may be preset by internal circuitry (not shown) to dictate the temperature conditions of the experiment whether they be heating, cooling, isothermal or a combination of these operating modes. The programmer, together with a computer 108, which manages the temperature averaging network, controls an amplifier 110 which supplies the main (or average) power to the sample and specimen. The differential power is supplied by a second amplifier 112 and is measured by a recorder 114. As shown, the circuitry includes control loops for the average temperature and for the differential power. This control system, which is solid-state digital throughout, is available commercially. The methods for operating it and for interpreting the results are known in the art. For a further description, see E. S. Watson et al., Analytical Chemistry, 36, 1233-8 (1964). See also U.S. Pat. Nos. 3,263,484 and 3,732,722.

The recorders 106 and 114 (FIG. 9) may be connected together at a terminal and plotted at 115 (FIG. 11) to produce a chart in which the variations in differential power are shown as a function of temperature. Such a DSC curve (as in FIG. 12a) constitutes the ultimate data output of the calorimeter portion of the instrument of the invention. A major advantage of the invention is that these calorimetric data may be correlated accurately with the X-ray diffraction data produced simultaneously by the diffractometer. Detailed insight into both structural and thermodynamic properties of the sample is thus possible.

(C) X-ray Geometry and Sample Mounting

The X-ray diffraction unit, as described and shown in FIG. 1, employs the geometry of the Guinier diffraction system and is equipped with a Huber curved focusing crystal monochromator. In the Guinier system, the sample 20 is located at one point along the focusing circle 41 of the diffractometer, while the detector 36 is at a different point along the circle. The X-ray beam 32 is converging as it passes through the sample but is not sharply focused on it. The focus is at a third point 116 along the circle 41. For practical reasons, the main beam may be terminated short of focus by an X-ray stop. The X-rays 34 diffracted by the sample reach true focus at points along the circle 41, within the detector 36. This Guinier geometry and its consequences have been considered at length by H. E. Göbel, Advances in X-Ray Analysis, 25, p. 315-324 (1982), and by T. G. Fawcett et al., loc. cit., 26 p. 171-180 (1982).

Figure 8:
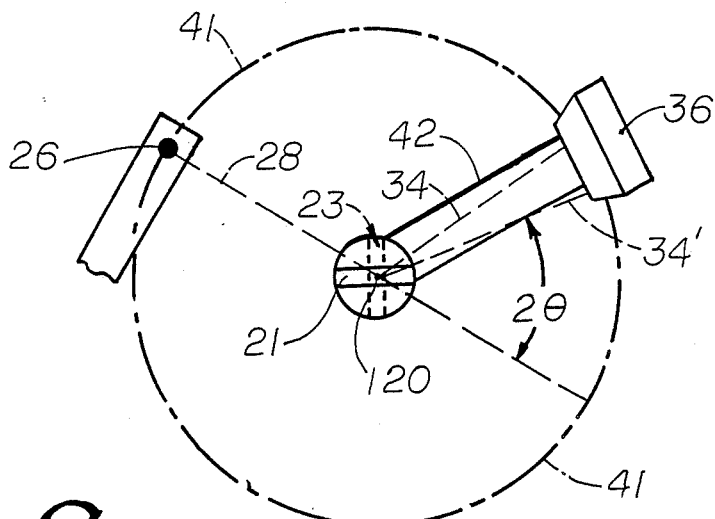
FIG. 8 is a schematic plan view of an alternative X-ray diffractometer using the geometry of the Bragg-Brentano system.

The Guinier geometry, while preferred, is not an essential requirement of the present invention. An alternative system is the Bragg-Brentano system, shown in FIG. 8. In this, the X-rays 28 are generated by the source 26 at a point which is itself along the focusing circle 41. The sample instead of being placed along the circle, is at its center 120. The sample may be in either a reflection 21 or transmission 23 position. X-rays diffracted from the sample are observed by the detector 36 at points along circumference of the focusing circle 41. This system has also been discussed by H. E. Göbel, Advances in X-Ray Analysis, 22, p.255–265 (1979).

Still another geometry satisfactory in the invention is that of a Debye-Scherrer camera, as in U.S. Pat. No. 4,076,981.

The X-ray geometry may be either wide angle or low angle, i.e. Statton, geometry. A line source, monochromatic and focused, is preferred. High resolution systems are helpful.

Figure 10:
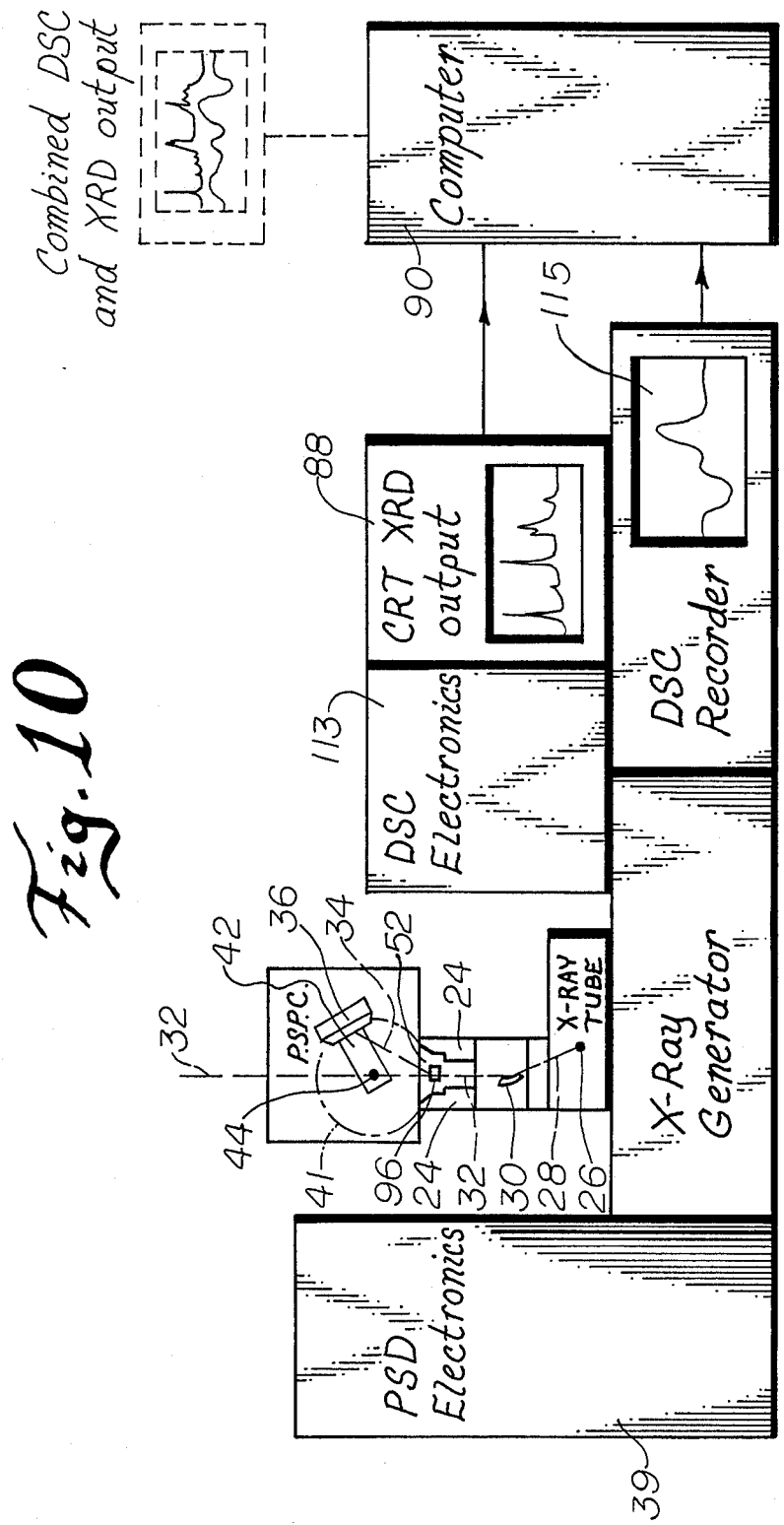
FIG. 10 is a schematic elevational section of an alternative apparatus configuration in which the X-ray beam is directed vertically upward.

An alternative diffractometer and DSC configuration is shown in FIG. 10 where the X-ray beam is passed vertically through the bottom of the sample holder. Such a configuration should provide better DSC sensitivity by n improved thermal contact; and an improved X-ray sensitivity by placing more sample specimen directly in the X-ray beam. In the FIG. 10 arrangement, simultaneous X-ray and calorimetric measurements are made using an enclosure block 24 which rests horizontally on a table. The X-ray beam 32 is directed vertically upward, entering through an inlet window in the bottom of the block and leaving through an exit window in the top of the block. Diffracted X-rays 34 pass through the exit window to the detector 36. The sample holder and holder support post have, e.g., hollow centers in order to allow for the transmission of X-rays. The sample rests in a pan (not shown) made of an X-ray transmitting material. Besides allowing for a number of geometric arrangements of the diffractometer, the invention also admits of various ways of mounting the sample and sample enclosure relative to the X-ray beam. For example, an alternative arrangement to FIG. 10 may utilize the Bragg-Brentano geometry (FIG. 8) for the diffractometer portion of the instrument in place of the Guinier transmission geometry (see FIG. 1). The Debye-Scherrer geometry is also feasible. Generally, any arrangement may be utilized which allows for impinging an X-ray beam on a sample and for observing the diffracted X-rays with a position sensitive detector.

(D) Gas-Reaction Calorimeter

The simultaneous observation of X-ray diffraction patterns and thermal data according to the invention may be used with advantage in studying phase transitions in solid or semi-solid samples while they are undergoing chemical reaction with a gas. Such studies are particularly valuable in investigating oxidation and reduction changes in complex metal oxide compositions used as heterogeneous catalysts. For this purpose, the arrangement shown in FIG. 11 may be employed.

Figure 11:
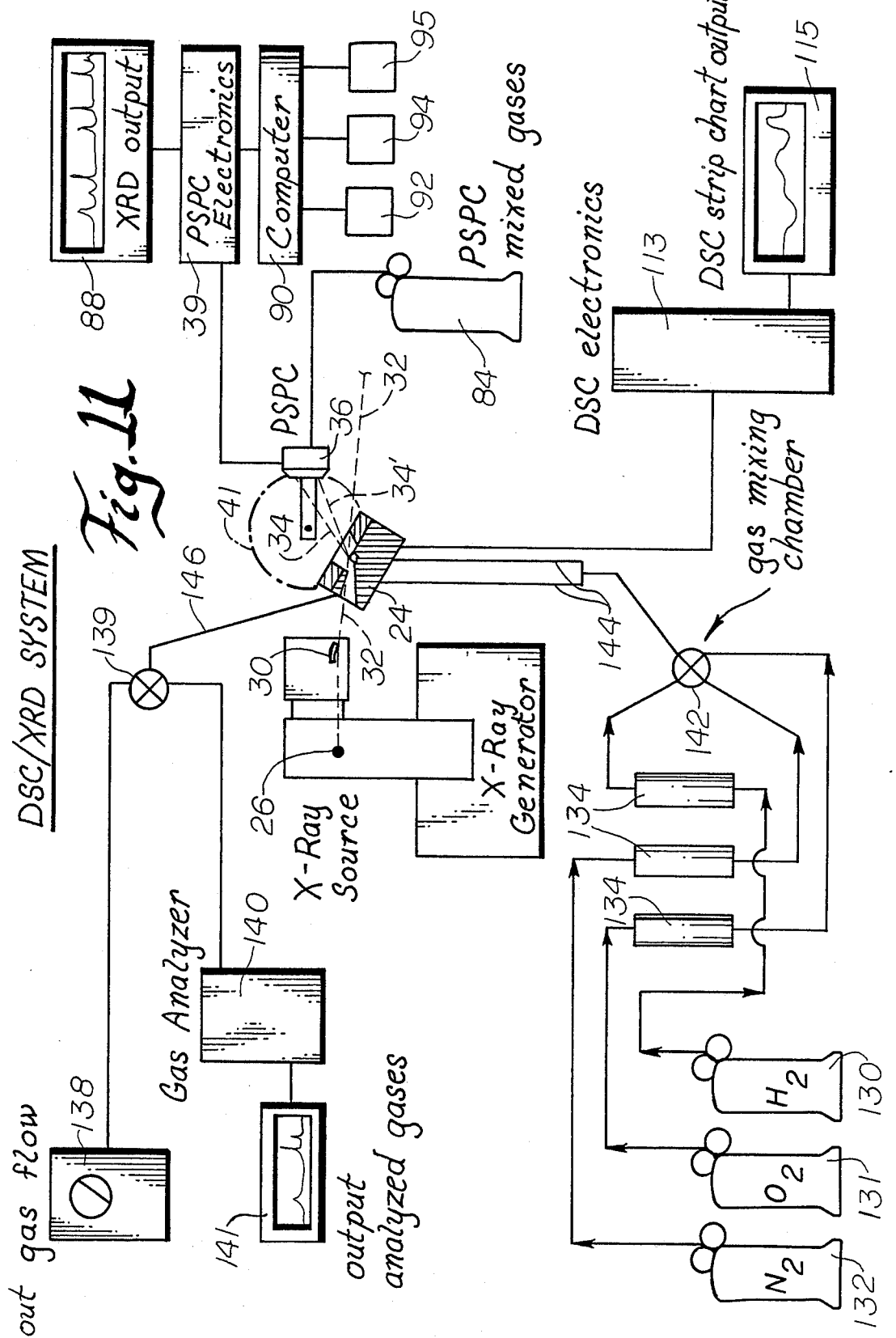
FIG. 11 is a schematic block diagram showing the relation of the control and recording systems of the entire apparatus according to the invention, and including a system for supplying gas to the sample enclosure and for analyzing effluent gas from the enclosure.
Figure 12A:
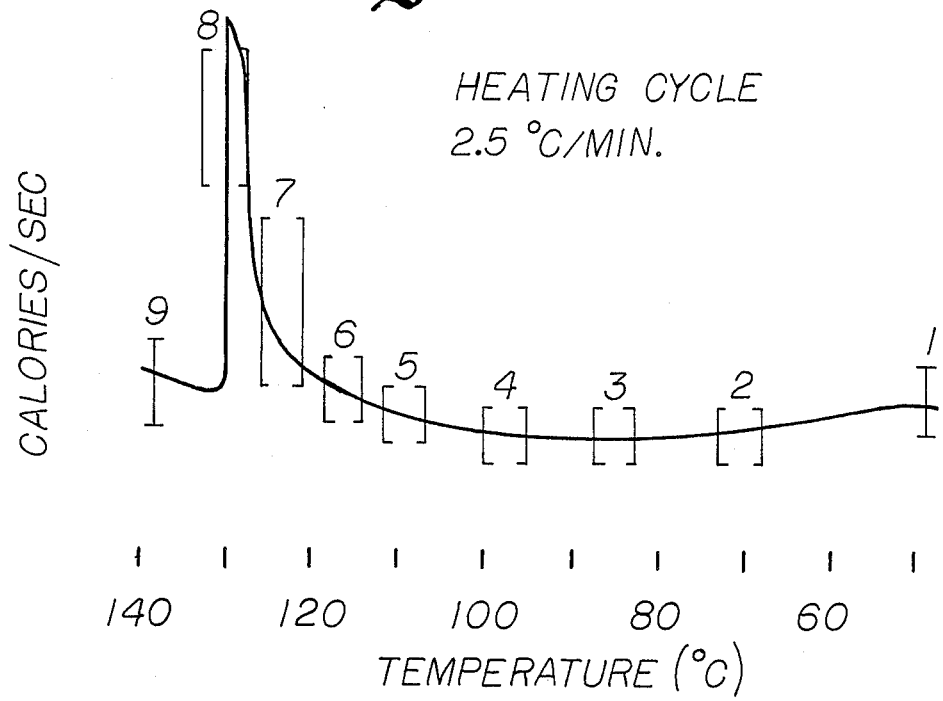
FIGS. 12a and 12b illustrate typical recordings of X-ray diffraction patterns (FIG. 12b) and corresponding DSC scans (FIG. 12a) made with the apparatus of the invention during a heating cycle.

The sample is placed in the sample block 24. In FIG. 11, this block is shown fitted with inlet ports 144 for admitting gas and an outlet port 146 for outflow. With the cover 48 in place, the only gas communication with the enclosure interior is through these ports.

The enclosure block 24 is positioned so that the X-rays 32 impinge on the sample. Diffracted rays 34 are received by the detector 36, and the resulting X-ray data are stored by the PSPC electronics 39 (described in detail with respect to FIG. 7) and displayed at the terminal 88, as previously described. Calorimetric signals from the enclosure as the temperature of the sample is scanned through a range to be studied are received by the DSC electronics 113 (described in detail with respect to FIG. 9) and displayed at recorder 115. A reactive gas, such as hydrogen 130 or compressed air or oxygen 131 from a cylinder, and a carrier gas, such as nitrogen from another cylinder 132, are used in the study. The gases flow through purifying and pressure regulating units 134. The flows merge at mixing chamber 142 and are then routed through the inlet ports 144 into the sample block 24 and into contact with the sample being studied. Gaseous reaction products leave through the outlet 146 to a flowmeter 138 or to a gas analyzer 140 by means of a switching valve 139. By comparing X-ray diffraction patterns with calorimetric signals, and with the indications of a gas analyzer 141, structural and chemical changes occurring in the sample during a scan can be identified and measured quantitatively.

(E) Alternative Thermoanalytical Apparatus

In the foregoing, the thermoanalytical equipment forming a part of the apparatus of the invention has been illustrated as a differential scanning calorimeter (DSC) of the power compensation type. This DSC is available commercially and known as the Perkin-Elmer Model DSC-2 (cf. U.S. Pat. Nos. 3,263,484 and 3,732,722). While this is well suited for the purpose, other types of differential scanning calorimeters known in the art may be employed, e.g., the commercially available duPont DSC, Mettler DSC 20, and Setaram Model DSC 111. Also useful are other thermoanalytical units not strictly calorimeters, such as differential thermal analyzers DTA's), e.g., The Mettler Model TA 10 and the duPont DTA.

As may be appreciated, the present invention is not restricted to any particular DSC or DTA. It is essential only that the analyzer have means for controlling the temperature of the sample being studied, and detector means for observing and recording a parameter indicative of the thermodynamic behavior of the sample during such change. "Thermodynamic Properties" refers broadly to calorimetric measurements of samples which can be determined or observed using a DSC or DTA instrument. This generally means for DSC, observing or measuring enthalpy change or specific heat capacity. For DTA experiments, it generally means or refers to observing or measuing qualitatively or semi-quantitatively exothermic and endothermic events of the samples under study as some function of temperature.

(F) Operation

While the manner of operating the apparatus of the invention is believed largely apparent from the foregoing description, it will, for added clarity, now be summarized.

The apparatus and method are useful for investigating simultaneously the thermodynamic and structural properties of materials. Single crystals and multicrystalline solids, inorganics, pharmaceuticals, and organics, as well as mixtures of materials, solid and semi-solid plastics en masse or as powder or film, and even liquids, may be studied to advantage.

In making a run, the sample 20 is placed in the sample holder assembly and rested on the sample holder 96. At the same time, a thermal reference specimen, in a reference pan 22', may also be placed in the enclosure on the reference holder 96'. As explained, the sample holder assembly 18 serves simultaneously to hold the sample in place relative to the X-ray diffractometer and to constitute the calorimetric chamber of the thermal analyzer.

With the sample and reference specimen in place, the sample holder assembly is positioned, by careful adjustment of its mount, so that the sample is in the path of the X-ray beam at a point on the focusing circle of the X-ray diffraction unit. The control and readout circuitry of both the diffractometer and calorimeter are then readied. If a gas atmosphere is to be circulated through the sample chamber, this too is readied. The controls are programmed to heat the sample and reference materials through the temperature range to be studied, and the rate of heating is also preset.

When everything is ready, the X-ray diffractometer and calorimeter are energized. Scanning then proceeds automatically. The diffractometer readout observes and records the angles and intensities of the X-rays diffracted from the sample. (These are measures of the angular positions of the diffraction peaks.) The record is presented by the plotter 94 on which the intensity is shown as a function of diffraction angle. The plot is repeated at frequent intervals which are time marked. The same data appear visually on the terminal 88 for instant attention by the operator.

Simultaneously, the scanning calorimeter observes and records both the temperature of the sample at each instant throughout the scan and the differential power, if any, required to hold the sample and reference temperatures in equilibrium. This record is also presented as a strip chart by the recorder 115, with the differential power shown as a function of temperature. The temperature line is also time-marked. If desired, the data may also be read visually on a terminal. The scan continues until the final preset temperature is reached, at which the run terminates.

To interpret the results, the analyst-operator compares the diffraction data and calorimetric printouts. The time markings on the printouts make possible the identification of simultaneous events. Thus, if the calorimeter printout shows a thermal event when some particular temperature was reached in the scan, the corresponding diffraction data will show what changes, if any, took place in the diffraction pattern at the same moment. The analyst studies the diffraction patterns and compares them with standard reference patterns known in the art as identifying various crystal species. The comparison allows identification of the phases involved in the change and the nature of the change.

In the apparatus of the invention, diffraction spectra and thermal events are detected and recorded so rapidly that entire scans over several hundred degrees Centigrade may be completed in a few minutes. The analyst can detect rapid crystallographic events, such as the appearance and disappearance of transitory phases having a brief life span, which would have escaped notice in the methods of the prior art. The analyst can also examine complex mixtures and detect and identify successive phase changes in individual components which take place over a temperature interval of only a few degrees. Chemical interactions of components of a multi-component mixture can be identified. Complex thermograms can be analyzed. In a single experiment, thermally induced structural changes, molecular orientation, crystallinity, stress, and strain as a function of temperature can all be studied, due to the precise temperature control and rapid speed of analysis of the instrument and method of the invention. Observations of these kinds have been impossible or the indications have been missed or misunderstood in prior art methods.

A further advantage of the invention may be brought into play when a thermal event or phase change has been observed in a first scan as occurring at a particular temperature, but the full details of the event are not clear. Another scan can be started, on the same or a fresh sample, but with the temperature rise stopped, or its rate slowed dramatically, when the temperature range in question is approached. Since only simple adjustment of the control circuitry is required, these temperature stops or rate changes can be made midway through a scan, whenever the need for change becomes evident. With the temperature steady or rising only slowly, extensive X-ray or thermal observations can be made to pick up critical details that may have been masked in the original rapid scan. This capability of interactive analysis, dynamic in that experimental parameters can be adjusted during an experiment, has made possible identification and characterization of structural and thermal correlations which have long been puzzling or even unknown.

The techniques of the invention are especially helpful when a reactive gas is being passed over a sample undergoing analysis. The scan can be stopped at any point, and the thermal and structural changes caused by reaction with the gas examined at length, while they are occurring.

Although the foregoing discussion has assumed that the temperature scans involve heating the sample, it is equally possible, in the invention, to scan downwardly in temperature. Observations can be started at an elevated temperature and cooling allowed to occur naturally or at a specified rate. To investigate ranges below room temperature, artificial cooling may be applied. The apparatus can be operated from temperatures as low as those of liquid nitrogen up to as high as 600° C. or more.

(G) Instrument Set-Up and Operation

Example 1

Construction and use of the invention may be further explained by the following example.

In the X-ray diffractometer (XRD) 17 (FIGS. 1 and 7), a Philips X-ray generator providing a Cu X-ray line source delivered the incident X-ray beam 28. A Guinier diffraction system with a Huber curved focusing germanium crystal monochromator was used to separate $CuK_{\alpha 1}$ from $CuK_{\alpha 2}$ and $CuK_\beta$ radiation. The resulting incident beam 32 converging on the sample was monochromatic (wave length=1.5406Å)

The detector 36 was a Braun curved position-sensitive proportional counter (PSPC). This detector, with its voltage supply 86 and multichannel analyzer 40 allowed simultaneous collection of diffracted X-rays over a range of about 20° ($2\theta$). Adjustably moving the detector about the post 44 to various positions allowed coverage of an accessible range of scattering angles, $2\theta$, of 0° to 70°.

The differential scanning calorimeter (DSC) used was a Perkin-Elmer DSC-2. The sample holder assembly 18 was constructed from the oven of the DSC-2. An X-ray inlet and an outlet were machined in the aluminum block and were covered with a 0.1 mm Mylar film for sealed operation. The sample 20, usually about 20 mg of material, was encapsulated in a 0.02 mm aluminum foil and placed in the sample holder 96. When X-ray intensity was not otherwise adequate, holes were punched in the foil to admit the full beam.

Operating parameters of the X-ray equipment were:

| X-ray source focus | Cu line source, long fine |
|---|---|
| Current | 20 mA |
| Voltage | 40 kV |
| PSPC gas | 90% argon, 10% methane |
| Gas pressure | 11–12 bar |
| Gas flow rate | 1.0 cc/hr |
| PSPC voltage | 4.0–4.4 kV |

The multichannel analyzer 40 collected the diffraction data with continuous observation made via a video terminal. After collection, X-ray diffraction data files were transferred via a commercial computer interface 87 to a hard disk on a PDP-11/34 computer for storage and analysis. At the end of an experiment, the patterns were processed in known manner by inputting to a peak-fitting and data reduction routine to obtain as parameters the peak position, area, half-width, etc. (cf. J. W. Edmonds et al., Advances in X-Ray Analysis, 22, p. 143 (1979).) Transfer time was about 30 seconds for a 1200 point data file.

In operating this equipment, the DSC was scanned at a preset speed, usually between 20° C./min and 1.25° C./min. X-ray diffraction patterns were taken at desired temperatures along the scan using collection times of less than five minutes per pattern.

Example 2

Figure 13A:
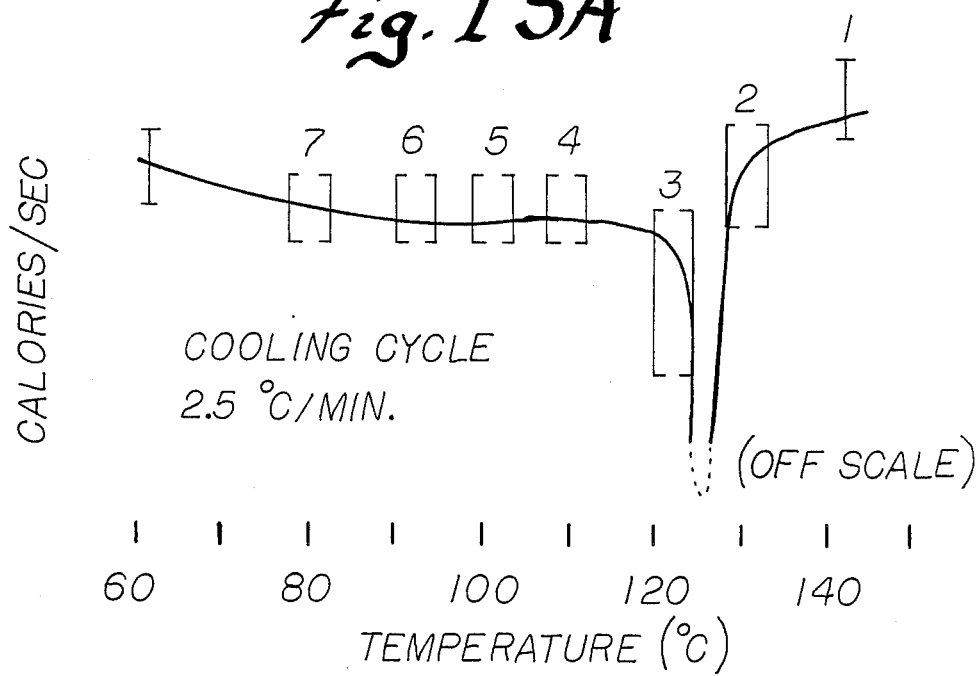
Figure 12B:
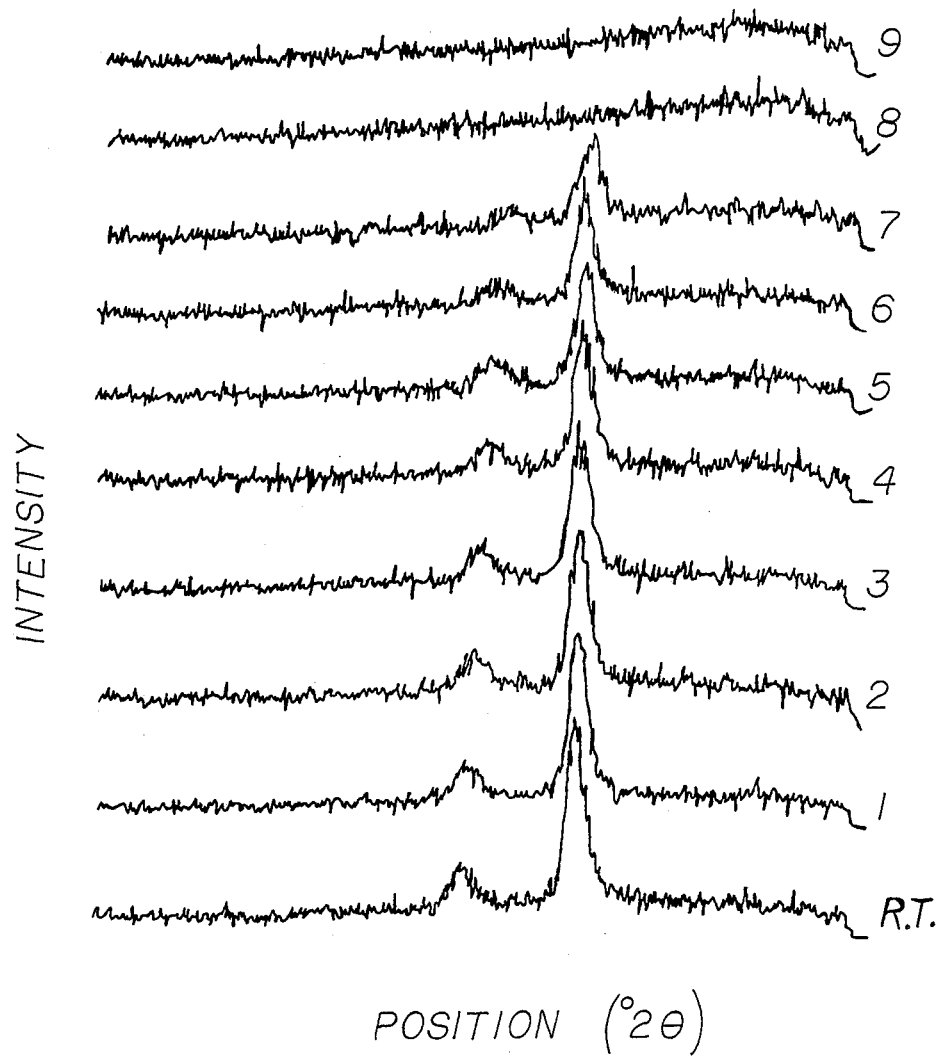

In a demonstration run a sample of polyethylene was heated to melting (FIGS. 12a and 12b) and then cooled back to room temperature (FIGS. 13a and 13b). The cycle was run at 2.5°/min and X-ray diffraction data was taken at two minute intervals. Correlation of the calorimetric and structural data shows the crystallinity of the sample as a function of temperatures and thermal (calorimetric) behavior.

Example 3

Figure 14A:
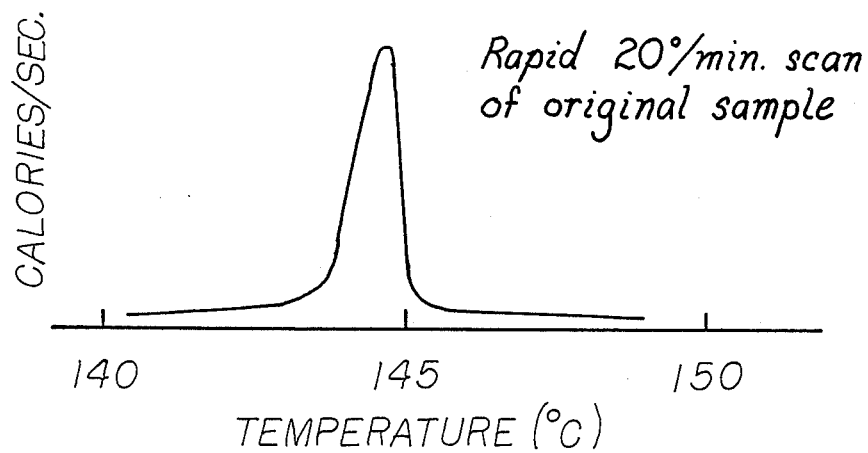
FIGS. 14a–14c illustrate DSC scans of a polymorphic organic compound before, during and after, respectively, a DSC/XRD experiment.
Figure 14C:
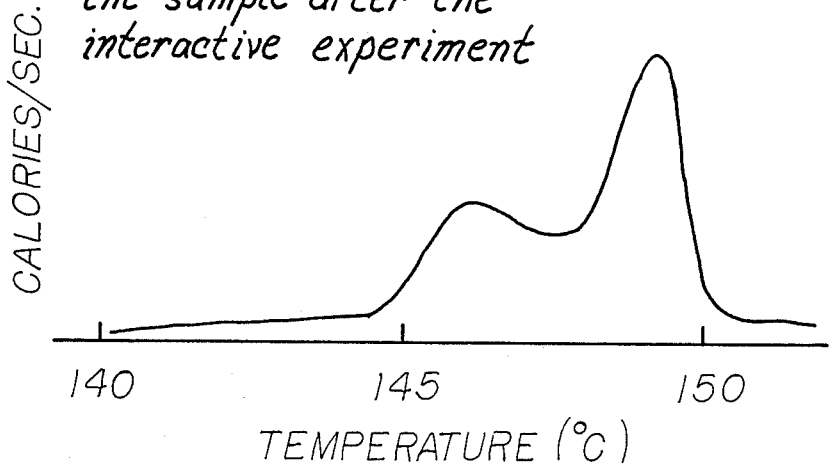
Figure 14B:
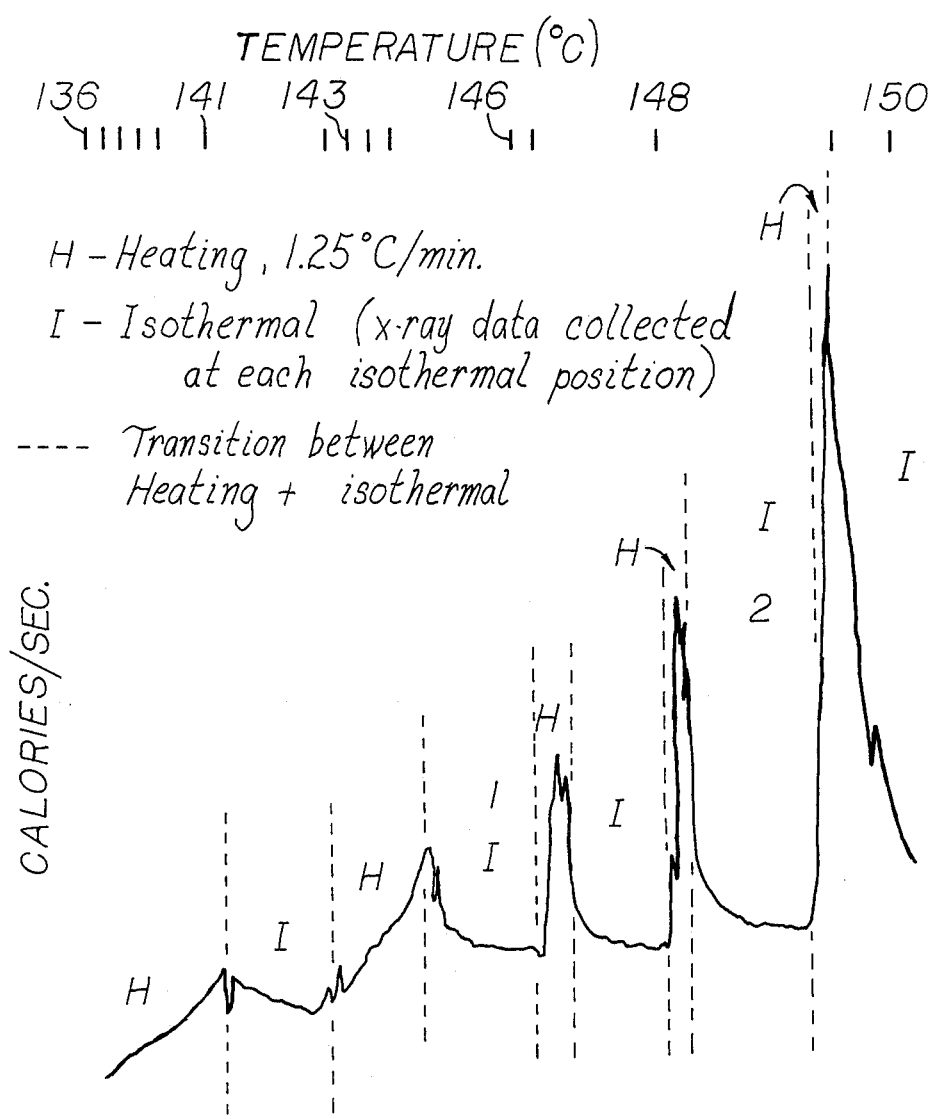

In another example, the DSC/XRD just described was used to investigate the interconversion of two organic polymorphs. This compound was known to exhibit two polymorphs with melting points differing by only 3° to 4° C. (FIGS. 14a–c). Previous analyses conducted in separate X-ray diffraction and differential scanning calorimetry laboratories showed that quantitation of the polymorphs by these techniques gave similar but not identical results. A DSC/XRD simultaneous experiment was conducted to study the differences in measurements. Previous work by hot stage microscopy had indicated that the lower melting form (II) might convert slowly to the higher melting form (I) upon heating, but there had been no clear understanding of the phenomenon, since microscopy could not differentiate between the two structures.

To evaluate the transformation, a sample of the pure lower melting form II was placed in the apparatus and an XRD scan made. The equipment was programmed to heat the sample slowly (1.25° C./min) until a melting endotherm was first observed on the DSC output at 145° C. (FIG. 14b). The temperature was then held constant at this value for three minutes while another XRD scan was taken (FIG. 15). The sample was then subjected to cycles, in each of which the temperature was raised slightly and then held level while another XRD scan was acquired, until the DSC showed the peak of the endotherm to have been reached. At this point, the temperature of the sample was held constant while more XRD scans were made. Finally, the temperature was lowered to 100° C. at a rate of 10° C./min, with an additional XRD scan being made. The entire run took no more than 25 minutes.

The data from this run are shown in FIG. 15. Comparison of the peaks in the diffraction spectrum of the initial scan at room temperature and the final one at 100° C. clearly shows that form II has been transformed to form I. It can also be seen that the two scans taken at the peak of the melt endotherm reveal small form I crystalline peaks remaining superimposed on the background. Analysis of these peaks using computerized peak-fitting routines showed that the final conversion of one phase to the other over the time of the experiment was about 88 percent complete.

The apparatus of the invention allowed precise temperature control which enabled the X-ray diffraction detector to observe the polymorphic interconversion. If the temperature was too high, both polymorphs would melt with no interconversion. If the temperature was too low, both materials would remain solid and not convert. Only if the temperature was within 145°–148° C., would interconversion take place. The interactive DSC data indicated to the experimenter the precise point of the endothermic melt and potential interconversion. The X-ray data were used to identify not only the interconversion, but the rate and completeness of the conversion. In summary, the DSC provided accurate temperature control and indicated the start of the endotherms, while the X-ray data identified a polymorphic interconversion and measured its rate. This was done on a single sample in a single experiment.

These results showed that previous quantitation of the polymorphs by DSC had been misinterpreted since not only did the polymorphs melt but they also interconverted during the experiment enabling a reconciliation of the previous DSC and XRD data.

(H) Further Uses of the Invention

The apparatus and method of the invention may be applied to study the interrelation of simultaneously occurring structural (e.g., crystallographic) and thermodynamic changes in materials in order to elucidate a wide variety of phenomena. In the plastics industry, the release of strains in the crystalline lattice of thermoplastics, such as molded polyethylene, during annealing has been examined; crystallite size, structure, and crystallinity all were measured and identified.

The combined DSC/XRD experiments described below were performed on the apparatus of the invention. Examples are given in which the simultaneous DSC/XRD experiment provided information which could not be obtained by either instrument alone.

Example 4

In the analysis of a polymer, the DSC data were characterized by a single endothermic peak at 185° C. However, the X-ray data taken simultaneously showed two structural events at the same temperature. One of the events was a crystallization (exothermic) of a portion of the sample. Therefore, the apparatus of the invention (DSC/XRD) showed that the observed DSC endotherm was in reality a combination of a larger endotherm with a smaller exotherm (i.e. two thermal events instead of one). The precise temperature control of the apparatus allowed for the X-ray detection and observation of the two events at the same temperature and elucidated the phenomena that the thermal transition at 185° C. was associated with two events of opposite heat flow (i.e., exo- and endotherm).

Example 5

A multicomponent product containing a blend of inorganics, organics and polymers was analyzed by the apparatus of the invention. In addition, the experiment was run so that the temperatures, atmospheric environment and heating times and rates simulated those of the commercial process. The sample was heated rapidly and cooled rapidly in a cycle from 23°–300° C. The entire experiment took 90 minutes. The DSC data show 3 events. Prior art comparisons of the multicomponent product to standards of the individual materials comprising the product could only identify the glass transition of the polymer. The other two events, an exotherm and an endotherm, could not be identified by comparison to standards. The DSC/XRD experiment showed that the exotherm was a crystallization of an organic in the polymer matrix. The endothermic transition was shown by the X-ray diffraction data to be the dissolution of the. organic in the sample matrix. The dissolution of the organic in the product occurred 70° C. below the melting point of the pure organic. When the experiment was conducted at either a different heating rate or under a different atmosphere, the exothermic and endothermic transitions were shifted by as much as 40° C. Therefore, to identify the structural nature of the thermal transition, both X-ray diffraction and calorimetric data had to be acquired simultaneously. Prior art instruments could not simulate either the speed or the temperature control of the apparatus of the invention. The experiments also showed how complex mixtures could be analyzed and how the chemical interactions among the components of the mixture (i.e., the in situ crystallization and dissolution 70° C. melting point) can be elucidated by the apparatus of the invention. Once again this analysis was critical since other experiments have shown that the impact strength of the product is affected by how the components blend in the mixture.

Example 6

Several copper compounds and copper compounds blended with additives were analyzed by the DSC/XRD apparatus of the invention for potential catalytic uses. The experiments usually consist of three parts: first, a careful preheating of the material in a controlled atmosphere (sometimes $N_2$, sometimes oxidative gas mixtures), second, reduction in a mixed $H_2/N_2$ atmosphere and finally, a catalyst regeneration program which involves both oxidation and reduction.

The DSC/XRD instrument provides careful temperature control in all phases of the experiment. In catalytic studies, this control can prevent unwanted runaway exothermic reaction (as in the reduction of metal catalysts). In the preheating stage, the DSC/XRD instrument provides precise measurement of thermal decomposition by correlating the DSC data with the observed X-ray diffraction patterns. On a multicomponent mixture, the correlated data identifies which material is being thermally changed and the magnitude and rate of that transition. Catalysts are commonly composed of the active material, a multicomponent substrate and other materials such as binders and pelletizing lubricants.

In the reduction experiments, which may be run isothermally, the DSC data indicate the start and the completion of the reductive exotherm. This is important since the X-ray diffraction data are a result of bulk transitions and are not sensitive to small changes which ca be seen in the DSC data (i.e., the initiation of the reduction and the very last steps of the completion of the reduction). In general, X-ray diffraction methods are sensitive to crystalline changes of one percent by total weight. The DSC data can detect noncrystalline changes in the material and some changes below one percent. The XRD data are used to determine which material or materials are being reduced. As in Example 3, experiments have been run where the reductive exotherm at an elevated temperature has been a combination of the simultaneous reduction of $CuO$, $Cu_2O$ and a copper salt to $Cu$ (metal) all in one step. Experiments have been run where >50 percent of the total reducible (or oxidizable) materials have been reduced (or oxidized) in less than 5 seconds. Therefore, the speed of the apparatus of the invention results in measured reaction rates with thermal-structural material identifications which have not been previously identified or measured.

In all phases of the catalytic cycles (oxidation, reduction, regeneration), times and temperatures can be optimized by the use of the invention. For example, if a high surface area catalyst is desired, the apparatus of the invention can be used to optimize the aforementioned cycles to get the desired physical properties in the shortest preparation time or in the best cost effective manner.

What is claimed is:

1. An instrument for studying structure of a sample material in a controlled environment and simultaneously studying energy changes in the sample material as a function of controlled temperature or atmospheric change, the instrument comprising:

a differential analyzer having means for determining energy changes in a sample material in comparison to a thermally heated reference contained in said analyzer and as a function of controlled temperature or atmospheric change, the analyzer having a sample holder assembly forming an enclosure relative to an external atmosphere which contains a thermally heated sample holder and which provides an environment in which the sample material is physically isolated from the external atmosphere so that a controlled temperature and atmospheric environment can exist about the sample material, a path defined through the sample holder assembly to and from the sample holder which is substantially transparent to X-rays to allow a beam of X-rays outside of the sample holder assembly to be impinged on the sample material within the sample holder assembly and to be diffracted effective for detecting the diffracted radiation, and an X-ray diffractometer including a source of an X-ray beam to impinge on the sample material through said sample holder assembly, and a position sensitive detector arranged for receiving diffracted radiation from the sample material.

2. An instrument according to claim 1 in which a monochromator is arranged with the X-ray beam source to provide a focused monochromatic beam.

3. An instrument according to claim 2 in which the X-ray source is a line source equipped with a Guinier diffraction system and a curved focusing crystal monochromator.

4. An instrument according to claim 2 in which the position sensitive detector has a focusing circle, the sample holder assembly is mounted so that a sample in the holder is at a point along the focusing circle, and the detector is mounted moveably along the circumference of the focusing circle and is connected to a multichannel analyzer.

5. An instrument according to claim 2 in which the position sensitive detector has a focusing circle, the sample holder assembly is mounted so that a sample in the holder is at a point in the center of the focusing circle, and the detector is mounted along the circumference of the focusing circle and is connected to a multichannel analyzer.

6. An instrument according to claim 1 in which the differential analyzer is a differential scanning calorimeter.

7. An instrument according to claim 1 in which the detector is a position sensitive proportional counter.

8. An instrument according to any of the preceding claims 2–7 in which there is included port means in the sample holder assembly for passing a gas into contact with the sample material retained by the sample holder and for removing the gas from the sample holder assembly to provide said controlled atmospheric environment.

9. An instrument according to claim 1 in which the differential analyzer is a differential thermal analyzer.

* * * * *

UNITED STATES PATENT AND TRADEMARK OFFICE
CERTIFICATE OF CORRECTION

PATENT NO. : 4,821,303

DATED : Apr. 11, 1989

INVENTOR(S) : Timothy G. Fawcett; William C. Harris, Jr.; Robert A. Newman; Lawrence F. Whiting; Frank J. Knoll It is certified that error appears in the above-identified patent and that said Letters Patent is hereby corrected as shown below:

Title page, Abstract, line 4, delete "and" and insert --are--(2nd occurrence)

Page 2, Col. 1, under "OTHER PUBLICATIONS", line 3, after "Chapter" delete "3.34" and insert --3.3.4--.

Col. 9, line 22, after "by" delete "n" and insert --an--.

Col. 12, line 50, delete "$CuK_{60\ 2}$" and insert --$CuK_{\alpha 2}$--.

Col. 15, line 25, after "the", first occurrence, delete the period (.).

Col. 16, line 6, delete "ca" and insert --can--.

Col. 18, Claim 8, line 2, after "2-7" insert --or 1--.

Signed and Sealed this

Twenty-ninth Day of May, 1990

Attest:

HARRY F. MANBECK, JR.

Attesting Officer

Commissioner of Patents and Trademarks